United States Patent
Shaughnessy

(10) Patent No.: US 7,551,712 B2
(45) Date of Patent: Jun. 23, 2009

(54) CT DETECTOR WITH NON-RECTANGULAR CELLS

(75) Inventor: Charles H. Shaughnessy, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 79 days.

(21) Appl. No.: 11/379,407

(22) Filed: Apr. 20, 2006

(65) Prior Publication Data

US 2007/0248207 A1    Oct. 25, 2007

(51) Int. Cl.
*H05G 1/00* (2006.01)
*H05G 1/64* (2006.01)

(52) U.S. Cl. .................................. 378/19; 378/98.8
(58) Field of Classification Search ............ 378/4, 378/19, 98.8; 250/368, 270.8–270.11
See application file for complete search history.

(56) References Cited

U.S. PATENT DOCUMENTS

| | | | |
|---|---|---|---|
| 4,817,123 A | | 3/1989 | Sones et al. |
| 5,138,167 A | | 8/1992 | Barnes |
| 5,510,622 A | * | 4/1996 | Hu et al. ..................... 250/367 |
| 5,680,427 A | * | 10/1997 | Dobbs et al. ................. 378/19 |
| 5,744,806 A | * | 4/1998 | Frojd .................... 250/370.09 |
| 5,994,694 A | * | 11/1999 | Frank et al. ................. 250/281 |
| 6,528,814 B1 | * | 3/2003 | Frank et al. .................. 257/30 |
| 6,963,631 B2 | * | 11/2005 | Brunnett ................... 378/98.8 |
| 6,256,239 B1 | | 7/2007 | Lai |
| 7,399,956 B2 | * | 7/2008 | Wong et al. ............ 250/231.14 |
| 2002/0176530 A1 | | 11/2002 | Okumura et al. |
| 2005/0061984 A1 | | 3/2005 | Hoffman |
| 2007/0086565 A1 | * | 4/2007 | Thompson et al. ............ 378/19 |

FOREIGN PATENT DOCUMENTS

| | | |
|---|---|---|
| JP | 06169911 A | 6/1994 |
| JP | 07084052 A | 3/1995 |
| WO | WO2005072612 A1 | 8/2005 |

* cited by examiner

*Primary Examiner*—Irakli Kiknadze
(74) *Attorney, Agent, or Firm*—Ziolkowski Patent Solutions Group, SC

(57) ABSTRACT

A CT detector cell is constructed to have diagonally oriented perimeter walls. With such a construction, the resulting CT detector comprised of such detector cells has improved spatial coverage (spatial density). The number of detector channels is also not increased despite the increase in spatial coverage. Moreover, the detector cells can be constructed without much variance from conventional fabrication techniques.

23 Claims, 5 Drawing Sheets

CT DETECTOR WITH NON-RECTANGULAR CELLS

BACKGROUND OF THE INVENTION

The present invention relates generally to CT detector design and, more particularly, to a CT detector with non-rectangular detector cells.

In conventional multi-row CT detectors, a two dimensional array of detector cells extend in both the x and z directions. Moreover, in conventional detectors, each cell of the array is constructed to have a rectangular-shaped active area. This active area is generally perpendicular to a plane of x-ray source rotation and, in the context of energy integrating scintillators, converts x-rays to light. The light emitted by each scintillator is sensed by a respective photodiode and converted to an electrical signal. The amplitude of the electrical signal is generally representative of the energy (number of x-rays x energy level of x-rays) detected by the photodiode. The outputs of the photodiodes are then processed by a data acquisition system for image processing.

As described above, each of the detector cells of the 2D array has a generally rectangular or square face, and is contiguous in both the x and z directions. As such, there is no overlapping in either of the x or z directions. This lack of overlapping places an upper limit on the spatial frequency of the region-of-interest, i.e., anatomy of interest, which can be resolved artifact free. A number of approaches have been developed to overcome the upper sampling limitations of conventional 2D detector arrays.

In one proposed solution, miniaturization efforts have led to a reduction in the size of the individual detector cells or pixels. Because the output of each detector cell corresponds to a pixel in a reconstructed image; conventionally, detector cells are also referred to as pixels. Segmenting the detector active area into smaller cells increases the Nyquist frequency but with the added expense of data channels and system bandwidth. Moreover, system DQE is degraded due to reduced quantum efficiency and increased electronic noise which results in a degradation in image quality.

In another proposed technique, focal spot deflection by deflecting the x-ray focal spot in the x and/or z direction at 2x or 4x the normal sampling rate has been found to provide additional sets of views. The different sets of views are acquired from slightly different perspectives which results in unique samples that provide overlapping views of the region-of-interest without subpixellation. A drawback of this approach is that a data acquisition system channel capable of very high sampling rates is required. Moreover, such a technique requires an x-ray source and associated hardware dedicated to rapid beam deflection. Ultimately, it has been found that focal spot deflection yields images with increased noise and reduced dose efficiency.

Another proposed approach to increasing sampling density of a CT detector involves the staggering of pixels. Specifically, it is has been proposed that sampling density may be improved by offsetting, in the z direction, every other channel or column of detector cells in the x direction. In one proposed approached, the offset is equal to one-half of a detector width. This proposed CT detector design as well as a more conventional CT detector design are illustrated in FIGS. 1-2.

As shown in FIG. 1, a conventional CT detector 2 is defined by a 2D array of detector cells 3 that are rectangular in their active area shape. As shown and described above, the array extends in both the x and z directions. In the CT detector design illustrated in FIG. 2, every other channel 4 (column) of detector cells 3 is offset. This provides an intermediate sample location between rows 5 increasing the number cells, decreasing cell size, or increasing the data acquisition system sampling rate. However, such a staggered design is difficult to fabricate since not all the rows are aligned.

Therefore, it would be desirable to design a CT detector that provides increased sampling density that is practical to fabricate yet does not over-burden the data acquisition system or necessitate an impractical number of data acquisition channels.

BRIEF DESCRIPTION OF THE INVENTION

The present invention is directed to a CT detector constructed to overcome the aforementioned drawbacks. The CT detector is comprised of detector cells having diagonally oriented perimeter walls. With such a construction, the CT detector has improved spatial coverage (sampling density). The number of detector channels is also not increased despite the increase in spatial coverage. Moreover, the detector cells can be constructed with a conventional cutting technique.

Therefore, in accordance with one aspect, the invention includes a detector cell having a generally planar active surface and a set of perimeter walls defining the generally planar active surface. The cell is constructed such that an angle of intersection formed between a pair of perimeter walls is acute.

According to another aspect of the invention, a detector for radiographic imaging is disclosed. The assembly comprises a detector array having a plurality of detector cells and is arranged along an x direction and a z direction perpendicular to the x direction. At least one detector cell has one edge in an x-z plane.

In accordance with another aspect, the invention is embodied in a CT system. The CT system includes a gantry that rotates about a plane of rotation, and an x-ray source disposed in the gantry and designed to project an x-ray beam. The system further has an x-ray detector situated parallel to the plane of gantry rotation and disposed in the gantry. The x-ray detector is configured to convert radiation projected by the x-ray source and attenuated by a subject to be imaged into a form that may be processed to reconstruct an image of the subject. The x-ray detector includes an array of detector cells, wherein each detector cell has a rhombus-shaped active area.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
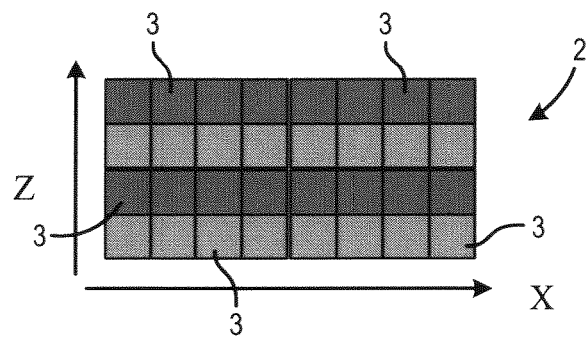
FIG. 1 is a plan view of a conventional rectangular CT detector matrix comprised of square-shaped detector cells.
Figure 2:
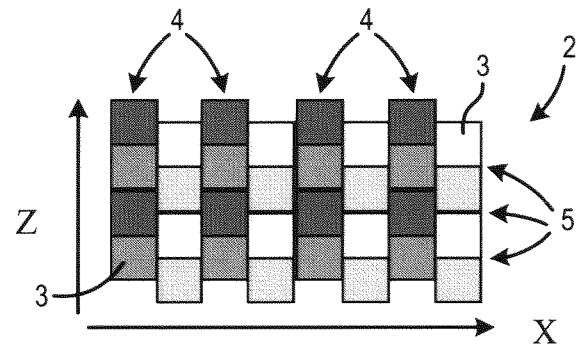
FIG. 2 is a plan view of CT detector matrix with staggered detector channels.

Referring to FIGS. 1 and 2, an exemplary computed tomography (CT) imaging system 10 is shown as including a gantry 12 representative of a "third generation" CT scanner. One skilled in the art will appreciate that the present invention is applicable with other configured CT scanners, such as those generally referred to as first generation, second generation, fourth generation, fifth generation, sixth generation, etc. scanners. Further, the present invention will be described to a CT detector cell geometry that is applicable with energy integrating cells as well as photon counting and/or energy discriminating cells.

Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center or plane of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As alluded to above, the present invention is directed to a CT detector comprised of individual detector cells or pixels. These cells are defined by an active surface or area and convert x-rays into a form that may be processed for image reconstruction. In this regard, the cells may, through a scintillator-photodiode combination, convert x-rays to light, detect the light, and provide an electrical signal to a data acquisition system for image reconstruction. The present invention, however, is not limited to scintillator-photodiode constructions. That is, as will be illustrated below, the present invention is also applicable with direct conversion detector cells that directly convert x-rays to electrical signal.

Additionally, the invention is applicable with conventional energy integrating cells as well as photon counting/energy discriminating cells. In a conventional integrating cell, the output of the scintillator or other x-ray conversion component is the product of the energy of the x-rays received and the number of x-rays received. Thus, there is no separation of the number of x-rays received from the energy level of the individual x-rays. Thus, it is possible, with energy integrating detector cells, for one cell to provide an output equal to that of another cell despite the one cell receiving more x-rays than the another cell. This equality in outputs is a result of the energy level of the x-rays received by the "another" cell being greater than the x-rays received by the "one" cell.

To provide photon count and/or energy discriminating information, CT detectors are increasingly being formed of energy discriminating and/or photon counting cells. These ED/PC detectors are capable of providing photon count and energy level information. Despite the differences between conventional energy integrating detectors and ED/PC detectors, there remains a need to improve spatial coverage/sampling density in both cases. Therefore, the present invention is applicable with both general types of detectors and, in fact, is not limited to a particular type of detector. Additionally, this invention is not limited to detectors for CT systems.

Figure 5:
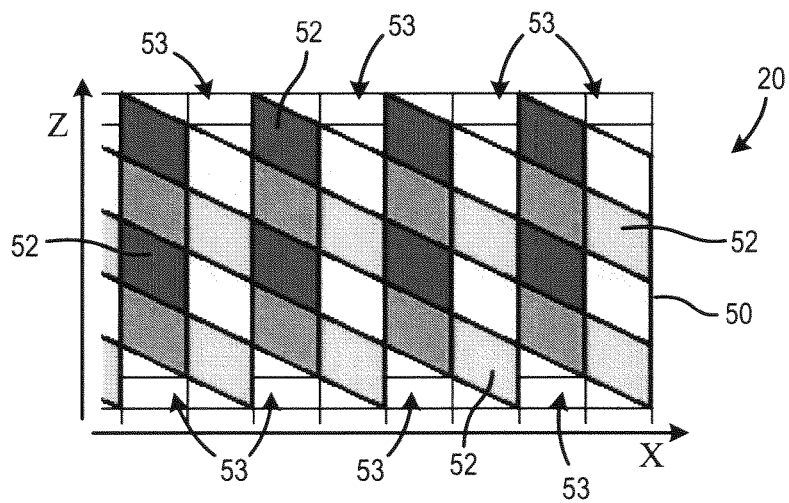
FIG. 5 is a plan view of a CT detector matrix with detector cells having diagonal edges according to one aspect of the invention.

To achieve a CT detector with improved spatial coverage, detector cells with diagonal edges or perimeter walls is proposed. An exemplary construction is illustrated in FIG. 5. As shown, a CT detector 20 is defined by an array or matrix 50 of detector cells 52. As shown, each detector cell 52 has a non-rectangular shape. This non-rectangularity increases the spatial coverage of the detector in the z direction. Despite the non-rectangularity in the geometry of each detector cell, as illustrated, the detector cells in each column (channel) are uniformly aligned with one another. This eases the fabrication process relative to the staggered-channel approach illustrated in FIG. 2.

As shown in FIG. 5, most of the detector cells are similarly shaped. However, because of the non-rectangularity of the detector cells, irregular shaped sections of the matrix must be accounted for. This is achieved by specially-shaped cells 53 that are constructed to "fill" the matrix. A skilled artisan will appreciate that each "specially-shaped" cell 53 may include multiple cells to fill the matrix.

Figure 6:
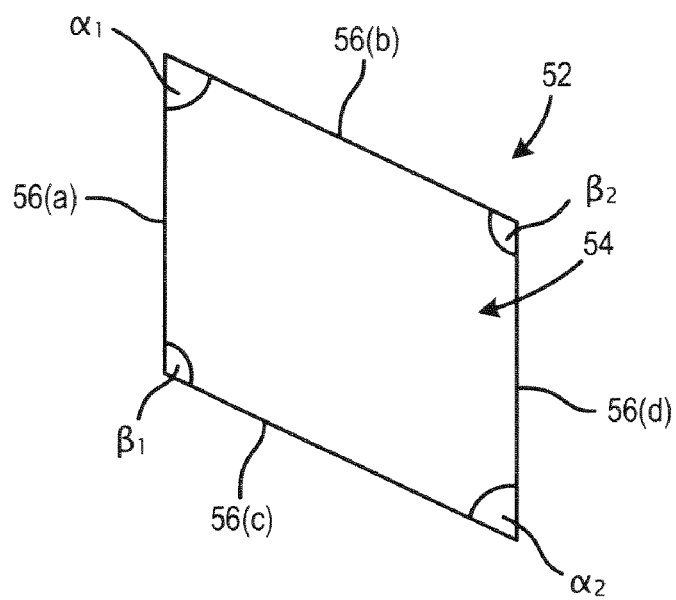
FIG. 6 is a plan view of a single exemplary detector cell in accordance with one aspect of the present invention.

Referring now to FIG. 6, a single exemplary detector cell 52 according to one aspect of the invention is shown. The detector cell 52 has an active area 54 that is generally parallel to the plane of x-ray projection (not shown) during data acquisition. In the exemplary illustration, the active area 54 is defined by four perimeter walls or edges 56. As shown, the exemplary cell has the shape of a rhombus. In this regard, the angle, $\alpha_1$, formed by the intersection of edges $56(a)$ and $56(b)$ is acute. Likewise, the angle, $\alpha_2$, between edges $56(c)$ and $56(d)$, is acute. Conversely, the angle, $\beta_1$, at the intersection of edges $56(a)$ and $56(c)$ and the angle, $\beta_2$, formed at the intersection of $56(b)$ and $56(d)$ are each obtuse. In short, edges $56(b)$ and $56(c)$ are not perpendicular to the plane of gantry rotation as in conventional rectangular shaped cells; however, channel edges $56(a)$ and $56(d)$ are perpendicular to the plane of gantry rotation. In this regard, the diagonal edges $56(b)$ and $56(c)$ extend in the x-z plane whereas edges $56(a)$ and $56(d)$ extend only in the z direction.

The geometry of the detector cell can be more generally described as follows. As shown, the z boundaries of the detector cell are formed by straight diagonal edges. Thus, with the cell pitch in the z direction referenced "a" and the cell pitch in the x direction referenced "b", the diagonal boundary makes an angle α with the x axis such that:

$$\tan(\alpha) = a/(2b) \quad \text{(Eqn. 1)}$$

For a=b, alpha is approximately 26.5 degrees. However, one skilled in the art will appreciate that the present invention is not limited to the case where a=b. For example, in one preferred embodiment, b=a√3/2. In this case, which was found to be particularly optimal for sampling density, alpha is 30 degrees. With an alpha of 30 degrees, a hexagonal lattice detector matrix or array would result. Other values for alpha are of course contemplated.

Figure 7:
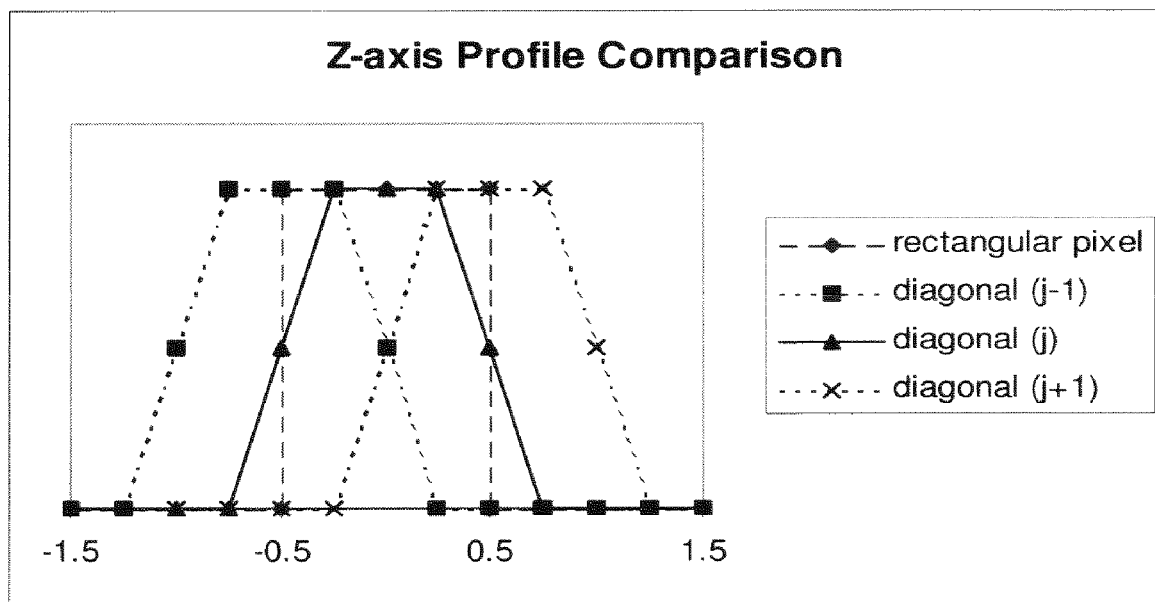
FIG. 7 is a graph illustrating a z-axis comparison of a conventional CT detector matrix and the CT detector matrix of FIG. 5.

As a result of edges 56(b) and 56(c) being in the x-z plane, the sampling density of the overall detector is improved, as illustrated in FIG. 7. Specifically, as illustrated, the z axis profile of a conventional rectangular detector cell is enveloped by the collective profiles of the diagonally edged cells illustrated in FIGS. 5-6.

Not only does the present invention provide a detector cell geometry with improved spatial coverage, it does so without requiring significant variants to conventional detector fabrication techniques. Specifically, the detector cell illustrated in FIG. 6 can be fabricated using two cuts in a cutting process. That is, after making a straight cut, i.e., edges 56(a) and 56(d), the wafer or bulk of x-ray converting material need only be rotated acutely a fixed degree of rotation followed by a second cut. Thus, instead of making four ninety degree cuts, a detector according to one embodiment of the present invention can be formed with two ninety degree cuts and two acute (less than ninety degree) diagonal cuts. This can be done without requiring a significant change to a typical cutting setup.

Figure 8:
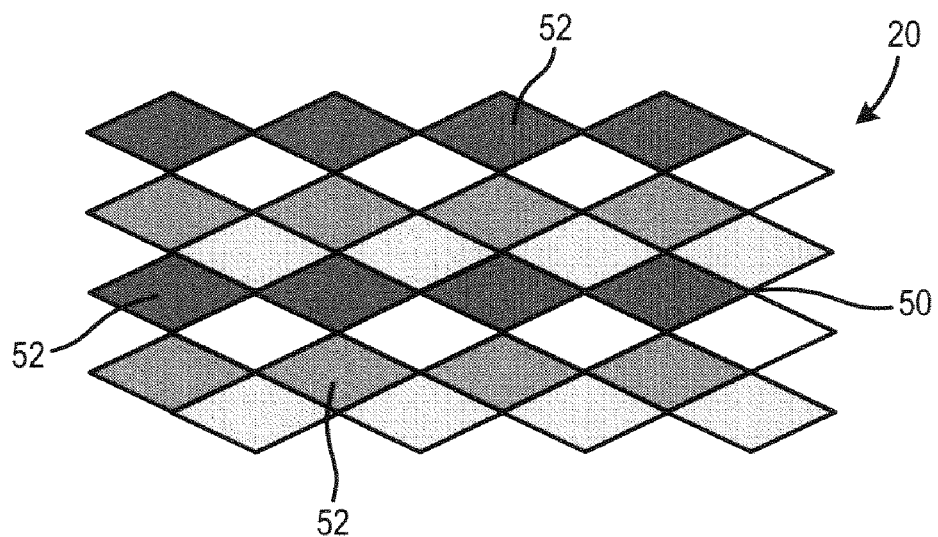
FIG. 8 is a plan view of a CT detector matrix with diamond-shaped detector cells according to another aspect of the invention.

Referring now to FIG. 8, a CT detector 20 having an array 50 of detector cells 52 shaped according to another embodiment of the present invention is shown. In this embodiment, each of the detector cells 52 is diamond-shaped. Thus, four diagonal edges rather than two, as in the cell shown in FIG. 6, define each cell. One advantage of the cell geometry illustrated in FIG. 8 is that there is substantial sample overlap in the x and z directions. Moreover, the z axis profile is narrower than that of conventional rectangular detector cells. One skilled in the art will appreciate that fabrication of the diamond-shaped detector cell can be carried out with a conventional wire-saw process.

Figure 9:
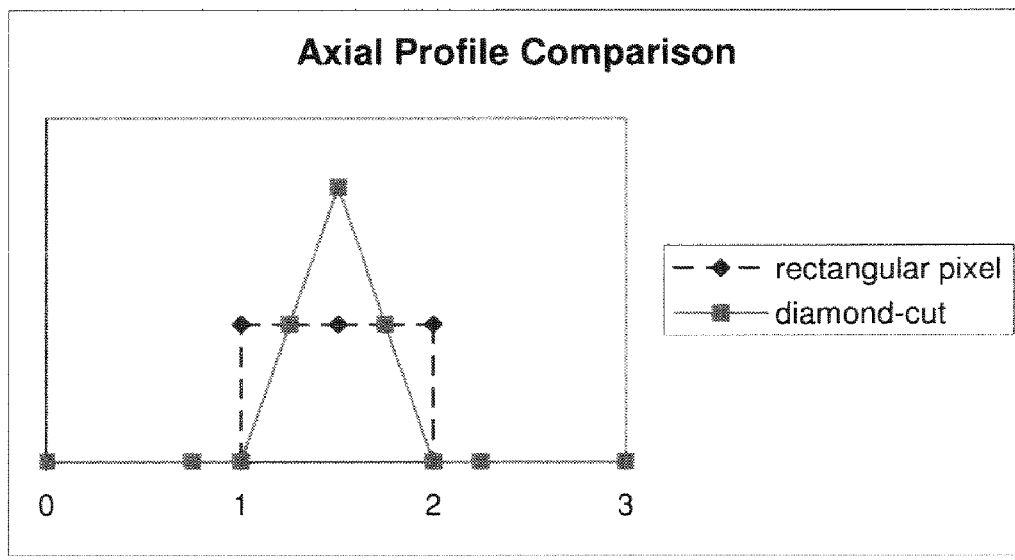
FIG. 9 is a graph illustrating a comparison in z-axis profile between a conventional rectangular-shaped detector cell and a diamond-shaped detector cell.

Referring to FIG. 9, the axial profile of a diamond-shaped cell relative to a rectangular-shaped cell is illustrated. As shown, notwithstanding the more narrow profile, the sampling coverage of the diamond-shaped cell is equal to that of a conventional rectangular-shaped cell.

Figure 3:
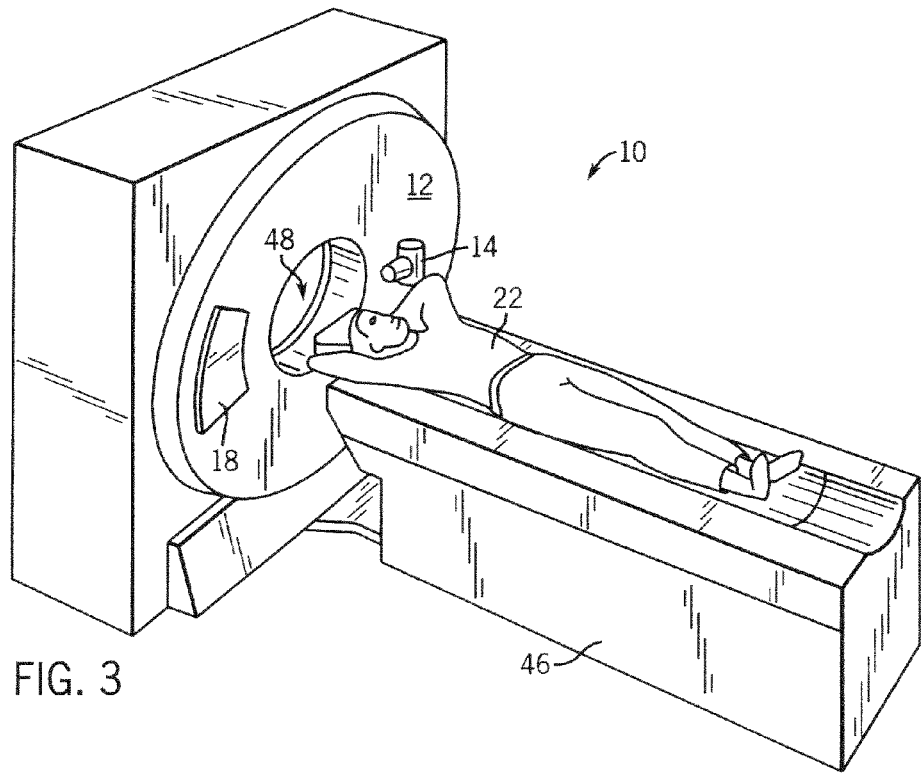
FIG. 3 is a pictorial view of a CT imaging system.
Figure 4:
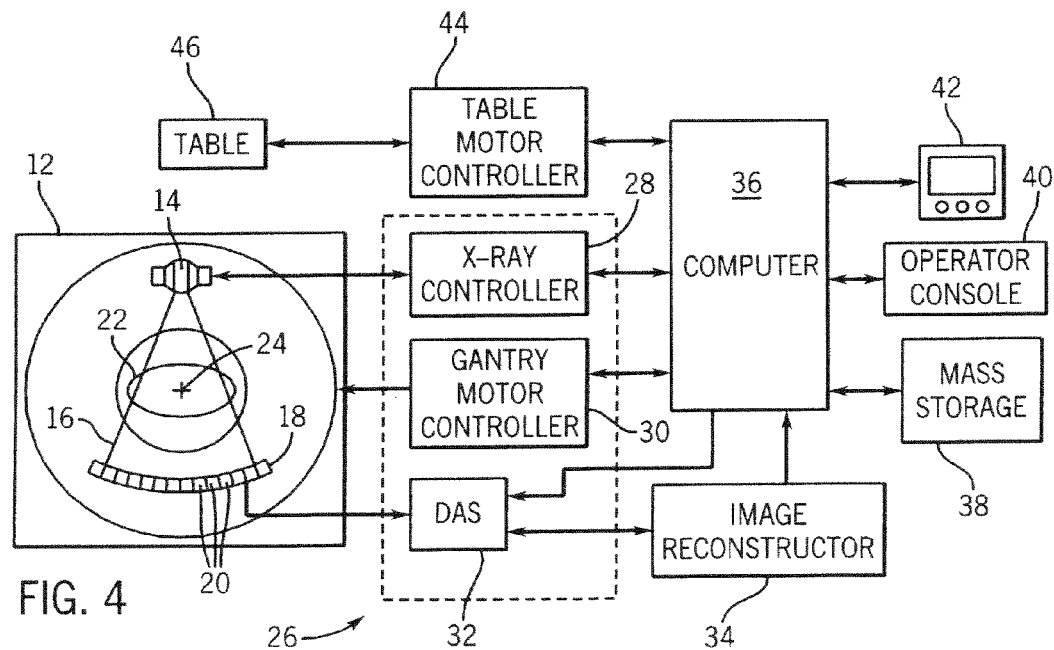
FIG. 4 is a block schematic diagram of the system illustrated in FIG. 1.
Figure 10:
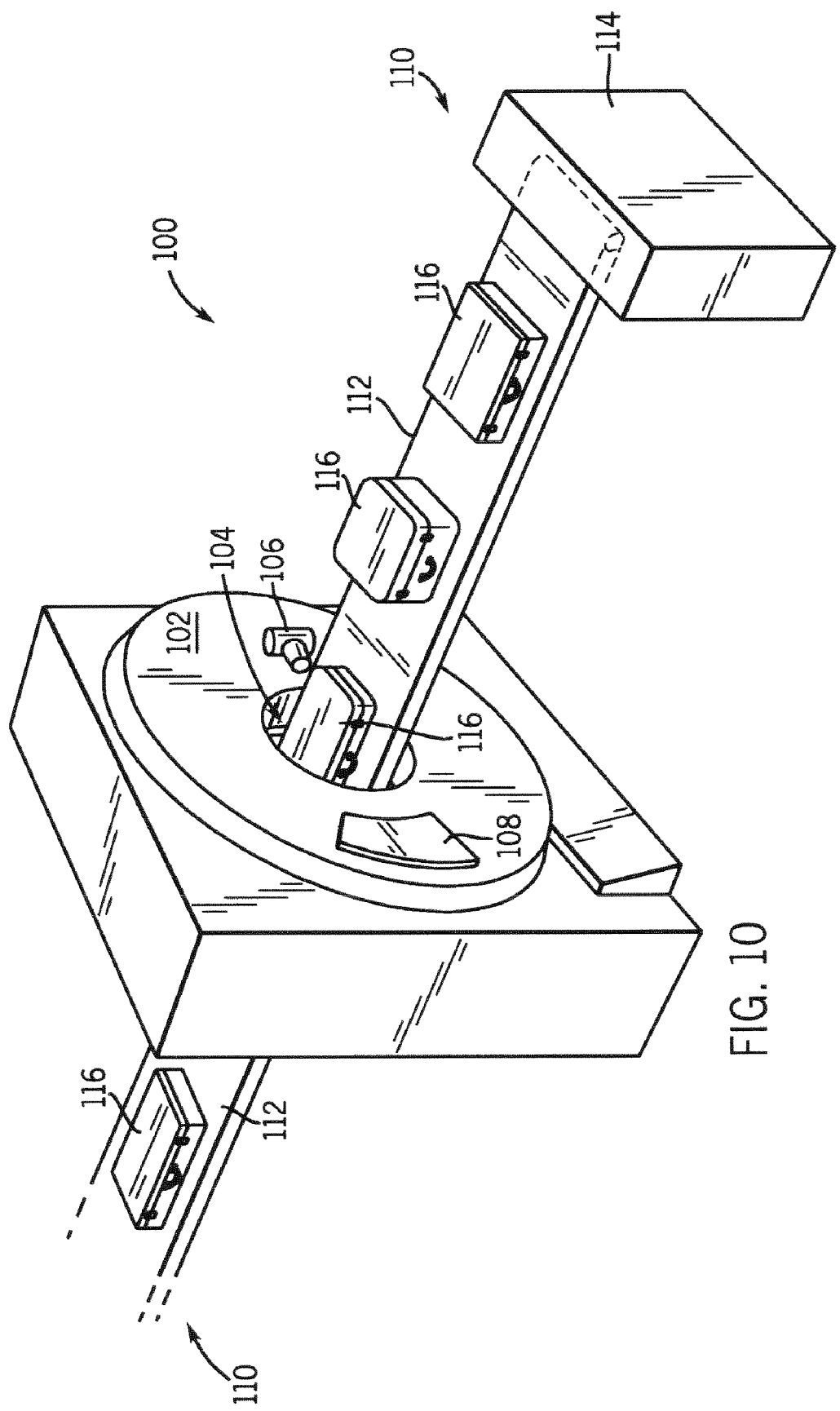
FIG. 10 is a pictorial view of a CT system for use with a non-invasive package inspection system.

The present invention may be incorporated in medical scanners, such as that shown in FIGS. 3-4, or non-medical scanners. Referring now to FIG. 10, package/baggage inspection system 100 incorporating the present invention includes a rotatable gantry 102 having an opening 104 therein through which packages or pieces of baggage may pass. The rotatable gantry 102 houses a high frequency electromagnetic energy source 106 as well as a detector assembly 108 having detector cells similar to those described herein. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

As noted above, the present invention is not limited to a particular type of detector cell. In this regard, it is contemplated that the invention can be applied to energy integrating, photon counting, or energy discriminating constructions. Thus, the invention is applicable with scintillators or direct conversion x-ray conversion material, charge collectors, such as photodiodes, charge-storage devices, charge collection anodes or cathodes, as well as, anti-scatter, collimator, and reflector grids.

As described herein and appreciable by one skilled in the art, the present invention provides a detector cell geometry that enables overlapping samples in the z and/or x directions without requiring additional data acquisition system channels. Moreover, the active area of each cell is equivalent to those of conventional detector cells. The detector cells can be fabricated with slight modification of a conventional wire-saw process; thus, fabrication costs are comparable to conventional detector cells. Moreover, since the diagonal and diamond-shaped cells described herein can be fabricated using wire-saw cuts of the same pitch, only a single wire-saw setup is required. Additionally, the detector cell is applicable with x direction flying-focal-spot deflection techniques, e.g., x-direction wobble, for improved sampling in the x direction. Further, for the embodiment illustrated in FIG. 6, the channel edges of each cell are aligned with the channel edges of each other detector cell in the channel. Thus, a conventional 1D scatter grid may be used. Also, one skilled in the art will appreciate that the present invention is applicable with CZT photon counting detectors. In such a case, the scintillator is not diced in a manner described above. The charge collection electrodes are formed with overlapping rows.

Therefore, the invention includes a detector cell having a generally planar active surface and a set of perimeter walls defining the generally planar active surface. The cell is constructed such that an angle of intersection formed between a pair of perimeter walls is acute.

A detector assembly is also disclosed. The assembly comprises a detector array having a plurality of detectors and is arranged along an x direction and a z direction perpendicular to the x direction. At least one detector of the plurality of detectors has one edge in an x-z plane.

The invention is also embodied in a CT system. The CT system includes a gantry that rotates about a plane of rotation, and an x-ray source disposed in the gantry and designed to project an x-ray beam. The system further has an x-ray detector situated parallel to the plane of gantry rotation and disposed in the gantry. The x-ray detector is configured to convert radiation projected by the x-ray source and attenuated by a subject to be imaged into a form that may be processed to reconstruct an image of the subject. The x-ray detector includes an array of detector cells, wherein each detector cell has a rhombus-shaped active area.

The present invention has been described in terms of the preferred embodiment, and it is recognized that equivalents, alternatives, and modifications, aside from those expressly stated, are possible and within the scope of the appending claims.

What is claimed is:

1. A detector cell comprising:
   a generally planar active surface;
   a scintillator body connected to the generally planar active surface and designed to convert x-rays received by the generally planar active surface to light; and
   a set of four perimeter walls defining the generally planar active surface, wherein an angle of intersection formed between a pair of the set of four perimeter walls is acute; and wherein the set of four perimeter walls is arranged to form a diamond-shaped active surface.

2. The detector cell of claim 1 wherein the diamond-shaped active surface comprises a rhombus-shaped active surface in an x-z plane, and wherein each of the four perimeter walls is oriented at an angle relative to each of the x-axis and the z-axis.

3. The detector cell of claim 2 wherein two of the four perimeter walls are in parallel with one another and the other two of the four perimeter walls are in parallel with one another.

4. The detector cell of claim 2 wherein the angle of intersection between any two perimeter walls that intersect one another is not ninety degrees.

5. The detector cell of claim 1 formed by two cuts of a scintillator wafer, the two cuts having a substantially similar wire pitch.

6. The detector cell of claim 5 further formed by making a first cut of the scintillator wafer at a given wire pitch and then, after making the first cut, rotating the scintillator wafer less than ninety degrees and making a second cut at the given wire pitch.

7. The detector cell of claim 1 wherein the angle of intersection is one of 26.5 degrees or 30.0 degrees.

8. A detector comprising:
a detector array having a plurality of detector cells and a plurality of filler cells configured to convert radiation into a form suitable for image reconstruction, the detector array arranged along an x direction and a z direction perpendicular to the x direction;
wherein the plurality of filler cells are positioned adjacent to a portion of the plurality of detector cells and constructed to fill spaces in the detector array; and
wherein at least one detector cell has one edge in an x-z plane, the one edge of the detector cell having an angle of intersection of between 20-40 degrees with an adjacent edge of the detector cell.

9. The detector of claim 8 wherein the at least one detector cell is defined by at least a pair of diagonally oriented edges.

10. The detector of claim 9 wherein the at least one detector cell is defined by four diagonally oriented edges.

11. The detector of claim 8 wherein the detector array provides greater sampling resolution than a detector array having edges that are only in one plane.

12. The detector of claim 8 wherein each detector cell is capable of providing energy discriminating and/or photon count information.

13. The detector of claim 8 wherein each detector cell is configured to directly convert x-rays to electrical signal.

14. The detector of claim 8 wherein each detector cell has a scintillator component that converts x-rays to light.

15. A CT system comprising:
a gantry that rotates about a plane of rotation;
an x-ray source disposed in the gantry and designed to project an x-ray; and
an x-ray detector situated parallel to the plane of rotation and disposed in the gantry, the x-ray detector configured to convert radiation projected by the x-ray source and attenuated by a subject to be imaged into a form that is capable of being processed to reconstruct an image of the subject, the x-ray detector including:
a plurality of detector cells each having a rhombus-shaped active area and arranged to form a detector cell array; and
a plurality of filler cells positioned adjacent to a portion of the plurality of detector cells and constructed to fill spaces in the detector cell array.

16. The CT system of claim 15 wherein each detector cell is diamond shaped.

17. The CT system of claim 15 wherein each detector cell has four perimeter edges, wherein an intersection of two perimeter edges is acute.

18. The CT system of claim 17 wherein an intersection of any two perimeter edges that intersect one another is not ninety degrees.

19. The CT system of claim 15 wherein each detector cell has a channel edge that is perpendicular to the plane of rotation.

20. The CT system of claim 15 wherein the x-ray source wobbles between a first position and a second position different from the first position during data acquisition.

21. The CT system of claim 20 where the first and the second positions are along an x-axis.

22. A method of x-ray detector construction, the method comprising the steps of:
fashioning a wafer of material designed to convert a first energy type to a second energy type different from the first energy type;
making a first cut of the wafer with a given wire pitch;
rotating the wafer less than ninety degrees; and
making a second cut of the wafer with the given wire pitch.

23. A detector cell comprising:
a generally planar active surface formed of a direct conversion x-ray conversion material configured to convert x-rays directly to electrical signals; and
a set of four perimeter walls defining the generally planar active surface, wherein an angle of intersection formed between a pair of the set of four perimeter walls is acute and wherein the set of four perimeter walls is arranged to form a diamond-shaped active surface.

* * * * *